United States Patent [19]
Karaki

[11] Patent Number: 5,224,382
[45] Date of Patent: Jul. 6, 1993

[54] TRANSMISSION TYPE SCANNING ACOUSTIC MICROSCOPE

[75] Inventor: Koichi Karaki, Hino, Japan

[73] Assignee: Olympus Optical Co., Ltd., Tokyo, Japan

[21] Appl. No.: 727,645

[22] Filed: Jul. 9, 1991

[30] Foreign Application Priority Data

Jul. 12, 1990 [JP] Japan ................................. 2-182805

[51] Int. Cl.⁵ ...................... G01N 29/06; G01N 29/24
[52] U.S. Cl. .................................... 73/606; 73/620; 73/642
[58] Field of Search ................. 73/599, 600, 602, 606, 73/607, 658, 620, 642

[56] References Cited

U.S. PATENT DOCUMENTS

| | | | |
|---|---|---|---|
| 4,367,648 | 1/1983 | Sinclair et al. | 73/620 |
| 4,972,715 | 11/1990 | Ohno | 73/620 |
| 5,085,081 | 2/1992 | Ohno | 73/620 |

FOREIGN PATENT DOCUMENTS

| | | | |
|---|---|---|---|
| 3909763 | 10/1989 | Fed. Rep. of Germany | 73/643 |
| 0010765 | 1/1986 | Japan | 73/606 |
| 0210943 | 9/1986 | Japan | 73/606 |

OTHER PUBLICATIONS

Acoustic Microscopy with Mechanical Scanning-A Review; Proceedings of the IEEE, vol. 67, No. 8, Aug. 1979; pp. 1092-1114.

*Primary Examiner*—Hezron E. Williams
*Assistant Examiner*—Rose M. Finley
*Attorney, Agent, or Firm*—Frishauf, Holtz, Goodman & Woodward

[57] ABSTRACT

A scanning acoustic microscope of the present invention comprises a high frequency transmitter for transmitting high frequency signal, first electric/acoustic conversion element for converting the high frequency signal to ultrasound, acoustic lens having an end surface to which the ultrasound is incident and a concave lens surface to which the incident ultrasound is exited, an ultrasound receiver having a flat receiving surface located in an opposed relation to the concave lens surface to allow the transmission of only that ultrasound substantially vertically incident to the receiving surface, second electric/acoustic conversion element for converting ultrasound which has been transmitted through the ultrasound receiver to an electric signal, and an image processing circuit for preparing an image in accordance with a reception signal delivered from the second electric/acoustic conversion element.

29 Claims, 4 Drawing Sheets

TRANSMISSION TYPE SCANNING ACOUSTIC MICROSCOPE

BACKGROUND OF THE INVENTION

1. Field of the Invention

The present invention relates to a scanning acoustic microscope of transmission type for forming an image with the use of ultrasound transmitted through a sample.

2. Description of the Related Art

A reflection type scanning acoustic microscope is known in the art which can observe a sample image, sample defect, etc., through the utilization of echo waves coming from a sample. This type of microscope cannot achieve a high image resolution when a sample is low in its reflectivity, such as a living cell. A transmission type scanning acoustic microscope has been conceived in the art which utilizes a contrast resulting from the absorption of ultrasound by a sample when it has been transmitted through the sample.

Figure 4:
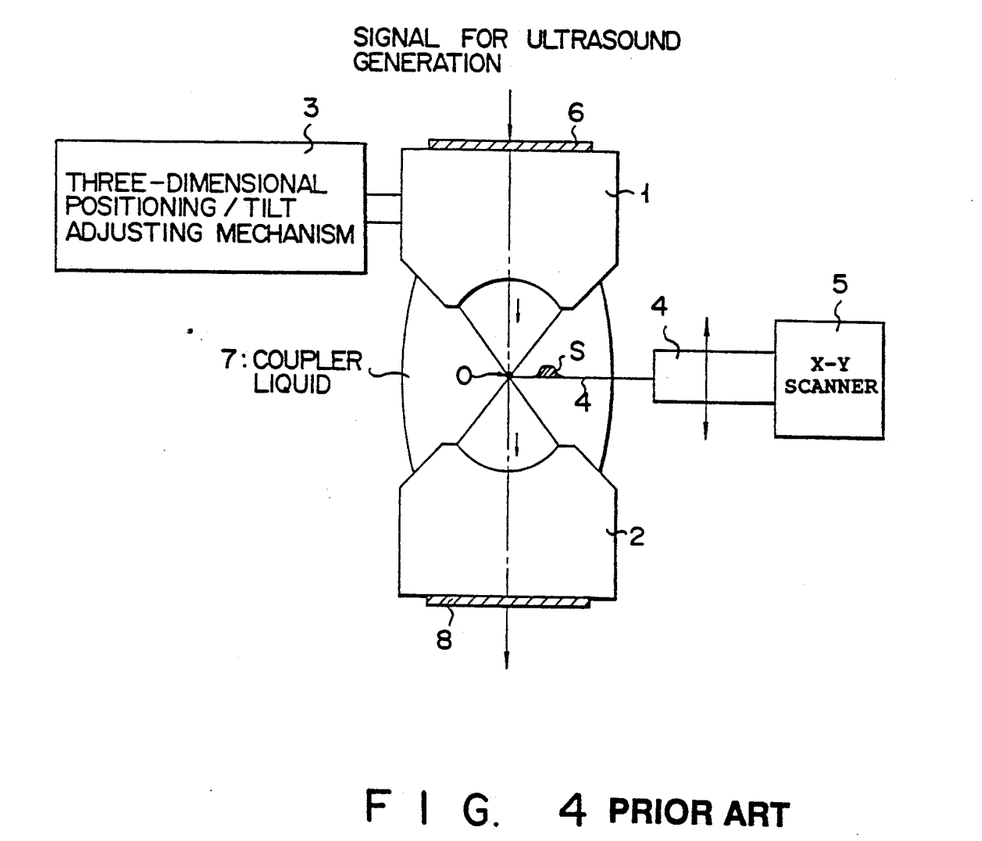

FIG. 4 shows one form of a transmission type scanning acoustic microscope.

In the transmission type scanning acoustic microscope, a transmission-side acoustic lens 1 and reception-side acoustic lens 2 are so arranged as to have their optical axes aligned with each other, the acoustic lens 1 being adapted to send ultrasound to a sample S and the acoustic lens 2 being adapted to detect ultrasound which has been transmitted through the sample S.

The positions and attitudes of these acoustic lenses 1 and 2 have to be so adjusted as to have their focal points and their optical axes aligned with each other, respectively. For this reason, one (the acoustic lens 2) of these acoustic lenses is fixed and the other acoustic lens 1 is supported by a known positioning/tilt adjusting mechanism 3. The sample S is located at a confocal point 0 between the acoustic lenses 1 and 2.

The sample S is placed on the surface of a thin film (not shown) having a uniform thickness, such as a Mylar sheet and loaded at the confocal spot 0. The thin film Mylar sheet is placed on a transfer mechanism 4 such that its basic end is movable in a direction of an optical axis. The transfer mechanism 4 is so held by an X-Y scanner 5 so that it can be moved in a plane perpendicular to the optical axis.

A high frequency signal for ultrasound generation is supplied to a transducer 6 which is provided on the transmission side acoustic lens 1. The ultrasound which is generated through its electric/acoustic conversion by a transducer 6 is converged by the transmission-side acoustic lens 1 at a spot where the sample S is located. By so doing, the ultrasound coming from the acoustic lens 1 is directed to the sample S through a coupler liquid 7.

Since the sample S is located at a focal spot of the reception-side acoustic lens 2, the ultrasound enters the reception-side acoustic lens 2 after it has been transmitted through the sample S.

Through the two-dimensional scanning of the sample S by the X-Y scanner 5, resultant ultrasound is acoustric/electric converted by a transducer 8 provided on the reception-side acoustic lens 2, generating an acoustic/electric conversion signal as an output signal. The output signal reveals a predetermined contrast corresponding to the inner structure of the sample in accordance with the level of absorption involved when the ultrasound is transmitted through the sample. By detecting the contrast data of the output signal it is possible to obtain an image corresponding to the sample S.

In the aforementioned confocal type scanning acoustic microscope, unless the two focal spots of the two acoustic lenses 1 and 2 have their positions aligned more accurately than their image resolution it is not possible to achieve a high degree of measurement of the order of the wavelength of the ultrasound. The resultant measurement is such that the plane resolution $d_{XY} = 1.0 \times F \times \lambda = 3.7$ μm; and
the depth resolution $dz = 2 \times F^2 \times \lambda = 7.5$ μm where
F number: 1.0
the working frequency of the acoustic
lenses 1, 2: 400 MHz
the coupler liquid 7: water.

It is required that the actual accuracy be empirically an order of magnitude greater than the above.

Thus much more accuracy as set out above is required in the three-dimensional positioning/tilt adjustment mechanism 3 in the conventional transmission type scanning acoustic microscope. Further, the positioning operation has been very difficult because high accuracy has to be maintained during scan.

SUMMARY OF THE INVENTION

A first object of the present invention is to provide a transmission type scanning acoustic microscope which can achieve the positional adjustment of an acoustic lens with not too high accuracy.

A second object of the present invention is to provide a transmission type scanning acoustic microscope which can improve the detection efficiency of ultrasound transmitted through a sample, without using a confocal arrangement, and hence can obtain a high resolution image.

In order to achieve the first object of the present invention, there is provided a transmission type scanning acoustic microscope which comprises a high frequency transmitter for transmitting a high frequency signal;

a first electric/acoustic conversion element for converting the high frequency signal to ultrasound;

an acoustic lens having an end surface to which the ultrasound coming from the first electric/acoustic conversion element is incident and a concave lens surface where the ultrasound coming from the end surface exits;

an ultrasound receiver having a flat ultrasound receiving surface located in an opposed relation to the concave lens surface to allow only the ultrasound which is vertically incident to the receiving surface to be transmitted therethrough;

a second electric/acoustic conversion element for converting the ultrasound which is transmitted through the ultrasound receiver to an electric signal and for delivering it as an output signal; and an image processing circuit for forming an image in accordance with the output signal delivered from the second electric/acoustic conversion element, in which the acoustic lens is located relative to the ultrasound receiver such that the ultrasound exiting out of the lens surface of the acoustic lens is reflected from the ultrasound receiver, converged at and near the sample located between the acoustic lens and the ultrasound receiver and, after the ultrasound converged there has been reflected from the lens surface of the acoustic lens, vertically falls on the ultrasound receiver.

A scanning acoustic microscope of the second invention comprises a high frequency transmitter for generating a high frequency signal;

an electric/acoustic converting element for generating ultrasound upon application of the high frequency signal thereto;

an acoustic lens having the electric/acoustic converting element provided at one end surface and a concave lens surface provided at the other end surface;

a phase conjugated mirror having a flat ultrasound receiving surface set in an opposed relation to the concave lens surface and receiving, at that receiving surface, the ultrasound from the acoustic lens and generating phase conjugate ultrasound as a wave whose travelling direction is reversed with the wave front being maintained; and an image processing circuit for receiving an output signal as a reception signal from the electric/acoustic converting element and for preparing an image from the reception signal, the reception signal being generated when the phase conjugate wave is incident to the acoustic lens via the lens surface and transmitted to the electric/acoustic converting element on one end surface of the acoustic lens, in which the acoustic lens is located relative to the phase conjugate mirror such that the ultrasound exiting out of the lens surface of the acoustic lens is incident to the ultrasound receiving mirror to allow the phase conjugate wave which is generated from the phase conjugate mirror in accordance with the incident ultrasound to be converged at and near a sample located between the acoustic lens and the phase conjugate mirror and transmission ultrasound which is obtained when the phase conjugate wave is transmitted through the sample to be reflected back from the lens surface of the acoustic lens and to be vertically incident to the ultrasound receiving surface of the phase conjugate mirror.

According to the first invention, the ultrasound coming from the acoustic lens is reflected from the ultrasound receiver and the reflected ultrasound is once converged at and near the sample site. That is, the reflected ultrasound is incident to the sample and transmitted ultrasound is incident on the lens surface of the acoustic lens and reflected there. The reflected ultrasound is converted to ultrasound parallel to the center axis (optical axis) of the acoustic lens and is vertically incident to the receiving surface of the ultrasound receiver.

Most ultrasound which is transmitted through the sample is vertically incident to the ultrasound receiving surface of the ultrasound receiver, and the ultrasound transmitted through the sample can very effectively be transmitted without need to use a confocal array.

According to the second invention, ultrasound coming front the acoustic lens is incident to the ultrasound receiving surface of the phase conjugate mirror. Upon receipt of the ultrasound, the phase conjugate mirror generates a reflection wave as a phase conjugate wave. The phase conjugate wave is converged at and near the sample site, that is, most of the phase conjugate wave is incident to the sample. The transmitted ultrasound is reflected from the lens surface of the acoustic lens, converted to parallel ultrasound as ultrasound parallel to the optical axis, and falls vertically on the ultrasound receiving surface. The phase conjugate mirror generates a phase conjugate wave corresponding to the vertically incident ultrasound. This is, most ultrasound transmitted through the sample is incident to the acoustic lens. The incident ultrasound propagates through the acoustic lens and reaches the electric/acoustic conversion element where it is converted to a reception signal.

Since most ultrasound which is transmitted through the sample is converted to the reception signal, the detection efficiency of the ultrasound transmitted through the sample can be improved without the need to employ the confocal array. No sever position adjustment accuracy is required because the microscope is not of a confocal type.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

The embodiment of the present invention will be explained below with reference to the accompanying drawings.

Figure 1:
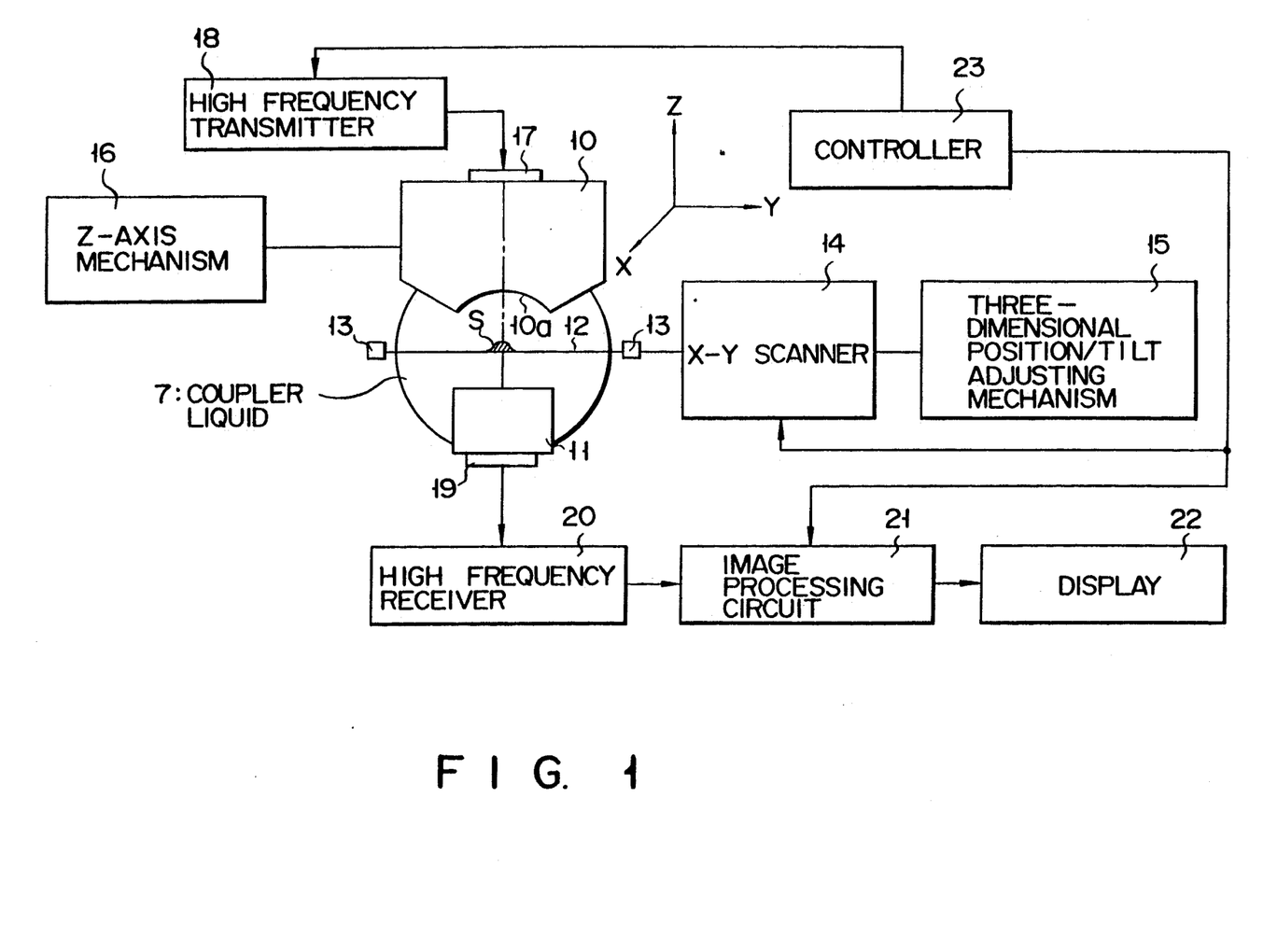
FIG. 1 is a block diagram showing a transmission type scanning acoustic microscope according to a first embodiment of the present invention

FIG. 1 is a block diagram showing a transmission type scanning acoustic microscope according to a first embodiment of the present invention.

In the transmission type scanning acoustic microscope, an acoustic lens 10 and ultrasound receiver 11 (hereinafter referred to as a flat detector) are arranged in an opposed relation, the acoustic lens 10 having a concave lens surface 10a and the flat detector 11 having a flat receiving surface 11a. A coupler liquid 7 is filed in the a space between the lens surface 10a of the acoustic lens 10 and the receiving surface 11a *of the flat detector 11*.

A sample support film 12 of uniform thickness is so arranged between the acoustic lens 10 and the flat detector 11 as to be held by a holding member 13. A sample S is placed on the sample support film 12.

The holding member 13 is held by an X-Y scanner 14 which in turn is held by a three-dimensional positioning/tilt adjusting mechanism 15. The sample support film 12 is moved in the X-and Y-directions, by the X-Y scanner 14, perpendicular to each other. The movement and attitude of the sample support film 1 in the X-, Y-and Z-directions are controlled by the adjusting mechanism 15.

The acoustic lens 10 is adjustably movable in the X-direction, by a Z-axis mechanism 16, corresponding to the direction of a center axis of the acoustic lens 10. A transducer 17 is mounted on one end of the acoustic lens 10 and receives a high frequency signal from a high frequency transmitter 18 and generate ultrasound through its electric/acoustic conversion. The acoustic lens 10 allows the exit of the ultrasound via its lens surface 10a and converges it at a spot (a focal position) determined by curvature of the lens surface 10a.

The flat detector 11 has a diameter substantially the same as the lens surface 10a of the acoustic lens 10 and is composed of a sound propagation medium similar to the acoustic lens 10. A transducer 19 is mounted on a surface opposite to the receiving surface 11a of the flat detector 11. The transducer 19 allows the ultrasound which has been received at the flat receiving surface 11a to be converted to an electric reception signal. The flat detector 11 and transducer 19 constitute an ultrasound detecting means.

The electric reception signal of the transducer 19 in the ultrasound detecting means is sent as an output signal to a high frequency receiver 20 where an image signal is produced. The image signal of the high frequency receiver 20 is sent to an image processing circuit 21. The image processing circuit 21 form an image corresponding to the sample S in accordance with an input image signal. The sample image can be displayed on the display 22. The operations of the high frequency transmitter 18, X-Y scanner 14, adjusting mechanism 15 and image processing circuit 21 are controlled by a controller 23 serving as a timing generator.

Figure 2:
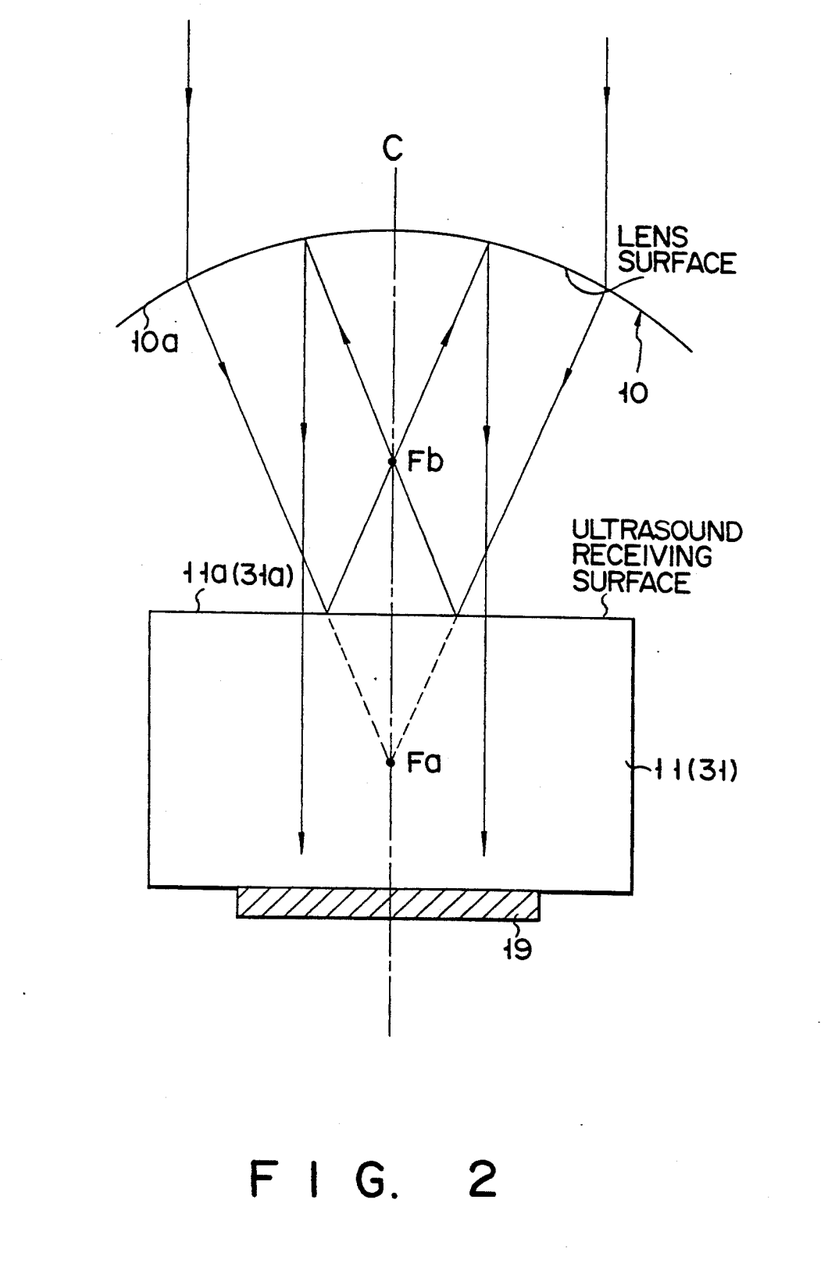
FIG. 2 is a view showing a positional relation of an acoustic lens to an ultrasound receiver in the first embodiment of the present invention.

According to the present invention, the acoustic lens 10 and ultrasound receiver 11 are as shown in FIG. 2.

The receiving surface 11a of the ultrasound receiver 11 is located substantially at an intermediate area between a refractive convergence focal point Fa and a reflective convergence focal point Fb of the acoustic lens 10 with a center axis C of the acoustic lens 10 set normal to the receiving surface 11a of the ultrasound receiver 11.

The "refractive convergence focal pint Fa" means a focal point at which reflected ultrasound arising from a sound velocity difference between the coupler liquid 7 and the sound propagation medium constituting the acoustic leans 10 is converged. The "reflective convergence focal point Fb", on the other hand, means a focal point at which, considering the acoustic lens 10 as a reflective concave mirror, ultrasound reflected after it has been incident upon the concave mirror in a direction parallel to that optical axis is converged in accordance with the curvature of the concave mirror.

In an ultrasound route between the acoustic lens 10 and the flat detector 11 as shown in FIG. 2, ultrasound coming from the acoustic lens 10 is converged at the reflective convergence focal point Fa and some of it is reflected on the receiving surface of the flat detector 11. The reflected ultrasound is once converged at the reflective convergence focal point Fb where the sample S is located. The converged ultrasound is reflected on the lens surface of the acoustic lens 10 to provide ultrasound parallel to the center axis C of the acoustic lens 10. The parallel ultrasound is incident in a direction perpendicular to the receiving surface 11a of the flat detector 11. Only those ultrasound components incident in a direction perpendicular to the receiving surface 11a of the flat detector 11 are detected by the transducer 19, the reason of which will be set out below.

That is, generally the sound velocity difference between the coupler liquid 7 and the ultrasound propagation medium (constituting the acoustic lens 10) or the flat detector 11 is very great. Let it be assumed that the sound velocity in the acoustic lens 10 or flat detector 11 is given by V1 and the sound velocity in the coupler liquid 7 is given by V2, a critical angle $\theta_0$ at reflection is:

$$\theta_0 = \sin^{-1}(V2/V1),$$

a value which is very small in practice.

For example, when water is used as a coupler liquid and sapphire is used as the acoustic lens, $$\theta_0 = \sin^{-1}(1.5/11.5) = 7.5°$$

From this it will be seen that the sound wave incident to the lens surface or the receiving surface at an angle of 7.5° to the optical axis is reflected there. Therefore, the sound wave reaching the transducer 19 for the flat detector 11 is restricted to that incident to the receiving surface within an angle range of below 7.5° to the optical axis.

The operation of the present embodiment will be explained below in more detail.

First the acoustic lens 10 is moved by the Z-axis mechanism 16 in an upward direction in FIG. 1 to provide an adequate operation spacing between the acoustic lens 10 and the flat detector 11.

Next a sample S placed on the sample support film 12 is inserted, by the adjusting mechanism 15, at an area between the acoustic lens 10 and the flat detector 11. With the sample S placed out of the optical axis of the acoustic lens 10, a coupler liquid 7 is filled at that area between the lens surface 10a of the acoustic lens 10 and the receiving surface 11a of the flat detector 11.

Then, a transmission trigger signal is sent from the controller 23 to the high frequency transmitter 18 where a high frequency signal is generated. While, at that time, a signal (reception signal) coming from the high frequency receiver 20 is being monitored, the acoustic lens is slowly moved toward the flat detector 11.

When the acoustic lens 10 is set relative to the flat detector as shown in FIG. 2, an abrupt increase in an amount of ultrasound is detected in that position by the transducer 19 on the flat detector 11. That is, the acoustic lens 10 is located at the aforementioned position relative to the fat detector 11 as shown in FIG. 2 In this connection it is to be noted that placing the sample S out of the optical axis is done because this prevents scattering of the ultrasound by the sample S.

The sample S is located by the adjusting mechanism 15 on the center optical axis C.

The controller 23 controls the X-Y scanner 14 such that, for example, the sample S is sequentially moved a predetermined amount in the X direction and, after this is done for one line, the sample S is stepwise moved in the Y direction and then sequentially again moved a predetermined amount in the X direction. At that time, a trigger signal is transmitted to the high frequency transmitter 18 each time the sample S is moved to a sequential position in the X direction. Ultrasound is generated through such a transmission of the trigger signal.

As a result, the ultrasound is incident from the acoustic lens 10 to each position (point) and the sample S is two-dimensionally scanned with ultrasound.

Since the sample S is located at the focal spot (position) of the acoustic lens 10, the ultrasound coming from the acoustic lens is converged at the spot of the sample S. The ultrasound is incident to the sample S where it is absorbed in accordance with the inner structure of the sample. By so doing, the ultrasound is transmitted through the sample S and is incident perpendicular to the receiving surface 11a of the flat detector 11 past the optical route shown in FIG. 2. Since the flat detector 11 allows the passage of the vertical incident ultrasound and most of its components reach the transducer 19.

That is, most of the transmission ultrasound components coming from the sample S during scan are converted by the transducer 19 to an electrical signal. The electric signal is supplied through the high frequency receiver 20 to the image processing circuit 21.

The image processing circuit 21 receives a reception signal on the basis of a timing signal coming from the controller 23, extracts information, such as a contrast, from the transmission ultrasound in the reception signal and converts it to pixel data. The pixel data is stored in an image memory, not shown. The controller 23 delivers a timing signal to the image processing circuit 21 in synchronism with the transmission trigger signal. When, therefore, the two-dimensional scanning of the sample S is completed, the image data of the sample is stored in the image data.

The image data is displayed on the display 22 as required.

According to the present embodiment, since the acoustic lens 10 is located relative to the flat detector 11 as shown in FIG. 2, the ultrasound coming from the acoustic lens 10 and reflected from the flat detector 11 is once converged at the sample spot Fa, reflected on the lens surface of the acoustic lens 10 and falls vertically onto the flat detector 11. It is, therefore, possible to detect the transmission ultrasound with a very high efficiency and to do so without using a confocal arrangement. It is also possible to improve the SN ratio of a reception signal coming from the high frequency receiver 20 and to hence obtain a high resolution image.

Further, the position accuracy of the acoustic lens 10 required can largely be alleviated as compared with that obtained from the conventional confocal type. The arrangement of the present microscope can be made simpler because adequate accuracy can be achieved with a simpler position adjustment mechanism.

A second embodiment of the present invention will be explained below.

Figure 3:
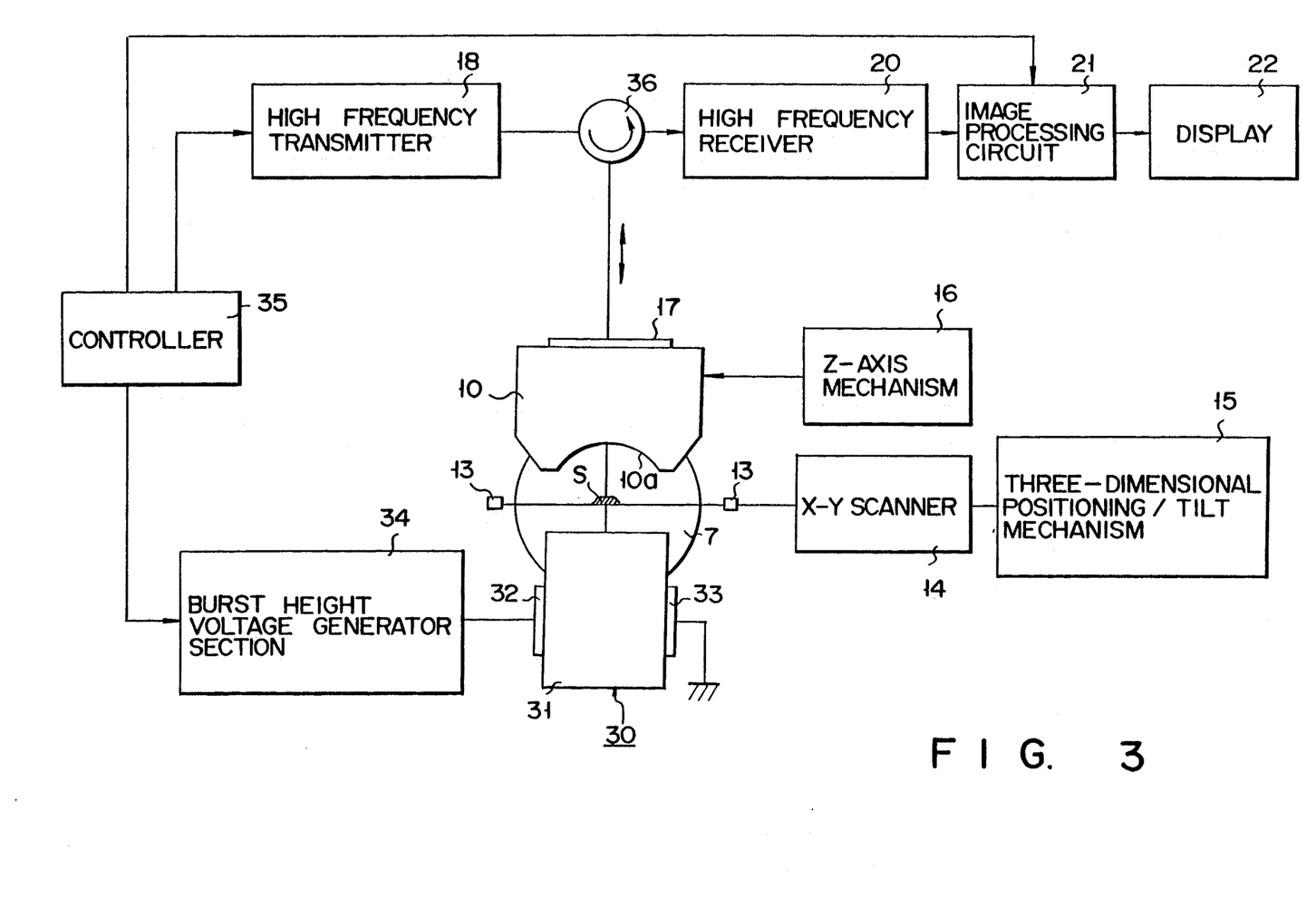
FIG. 3 is a functional block showing a transmission type scanning acoustic microscope according to a second embodiment of the present invention and FIG. 4 shows a functional block of a conventional transmission type scanning acoustic microscope.

FIG. 3 is a view showing a general arrangement of a transmission type scanning acoustic microscope according to a second embodiment of the present invention. In FIG. 3, identical reference numerals are employed to designate parts or elements corresponding to those shown in FIG. 1.

In the embodiment shown in FIG. 3, a phase conjugate mirror 30 is arranged in an opposed relation to a lens surface 10a of an acoustic lens 10. The phase conjugate mirror 30 comprises a nonlinear piezoelectric mirror 31 composed of, for example, a $Ninb_3O_5$ having an acoustic nonlinear characteristic and including a flat-like receiving surface 30a provided in an opposed relation to the lens surface 10a of the acoustic lens 10, a pair of electrodes 32, 33 arranged in an opposed relation with the nonlinear piezoelectric element 31 sandwiched therebetween, and a burst height generator 34 for applying a high frequency voltage composed of burst voltage waves to one (34) of these electrodes.

The other electrode 33 on the nonlinear piezoelectric element 31 is grounded. The burst height voltage generator 34 is operated based on an instruction coming from a controller 35.

The phase conjugate mirror 30 has a function of generating a wave (phase conjugate wave) whose travelling direction is reverted while maintaining the wave front of incident light.

A high frequency signal sent from a high frequency transmitter 18 is delivered via a circulator 36 to a transducer 17 on the acoustic lens 10 and ultrasound again entering the acoustic lens 10, after being converted by the transducer 17 to an electric signal, is sent via the circulator 36 to a high frequency receiver 20.

The acoustic lens 10 is located relative to the phase conjugate mirror 30 in a relation shown in FIG. 2. That is, the flat surface 31a is located substantially at an intermediate position between a refractive convergence focal point Fa of the acoustic lens 10 and a reflective convergence focal point Fb with the flat surface 31a set perpendicular to a center axis C of the acoustic lens 10.

In the arrangement thus described, ultrasound coming from the acoustic lens 10 is reflected on the flat surface 31a and the reflected wave is converged once nearly at a site of a sample S. The ultrasound transmitted through the sample S is reflected on the lens surface of the acoustic 10, converted to ultrasound parallel to the center axis C, and vertically falls on the flat receiving surface 31a of the phase conjugate mirror 30.

The phase conjugate mirror 30 generates a phase conjugate wave corresponding to the vertically incident ultrasound, that is, delivers, to the acoustic lens 10 side, ultrasound (phase conjugate wave) corresponding to that ultrasound reversed in its travelling direction which has vertically been incident to the receiving surface 31a, of the mirror 30. As a result, transmission ultrasound travelling parallel to the center axis C which has been converted by the phase conjugate mirror 30 to a phase conjugate wave is incident to the acoustic lens 10 and reaches the transducer 17. Then the transmission ultrasound is output, as a reception signal, to the image processing circuit 21.

The positional adjustment of the acoustic lens 10 relative to the phase conjugate mirror 30, two-dimensional scanning of the sample S, and so on, are the same as in the first embodiment and are, therefore, omitted.

According to the present embodiment since most ultrasound which has been transmitted through the sample S is converted to a reception signal without the need to adopt a confocal arrangement, it is possible to obtain a high resolution image and hence a simpler microscope of high measuring accuracy.

According to the present embodiment, since an ultrasound wave passes through the sample S, and near it, four times twice in a forward journey and twice in a backward journey, a disturbing wave front is generated due to an uneven surface of the sample S, but, due to the presence of the phase conjugate mirror, the disturbance is fully recovered theoretically. Thus a signal obtained reflects an absorption level alone, gaining a high accurate, measuring value.

Additional advantages and modifications will readily occur to those skilled in the art. Therefore, the invention in its broader aspects is not limited to the specific details, and representative devices, shown and described herein. Accordingly, various modifications may be made without departing from the spirit o scope of the general inventive concept as defined by the appended claims and their equivalents.

What is claimed is:

1. A scanning acoustic microscope comprising:
 means for generating a high frequency signal;
 first electric/acoustic conversion means for converting the high frequency signal to ultrasound;
 an acoustic lens having an end surface to which the ultrasound coming from the first electric/acoustic conversion means is incident and a concave lens surface where the ultrasound coming from the end surface exits;
 beam conversion means having a flat surface for reflecting at least a portion of the ultrasound exiting from the acoustic lens and for transmitting therethrough an other portion of the ultrasound exiting from the acoustic lens, the flat surface being positioned so that most of an ultrasound which is transmitted through a sample is converted to parallel beams in cooperation with the concave lens surface of the acoustic lens;
 an ultrasound receiver having a receiving surface that allows the ultrasound which is converted by the beam conversion means into the parallel beams, to be incident thereon substantially vertically so that said parallel beams are transmitted therethrough;
 second electric/acoustic conversion means for converting ultrasound which is transmitted through the ultrasound receiver surface of the ultrasound receiver to an electrical signal and for generating a reception signal; and
 image forming means for forming an image corresponding to the reception signal output from the second electric/acoustic conversion means.

2. The microscope according to claim 1, wherein:
 the receiving surface of the ultrasound receiver is so formed as to be the same as the flat surface of the beam conversion means; and
 the second electric/acoustic conversion means is provided on an end surface oppositely facing the receiving surface of the ultrasound receiver.

3. The microscope according to claim 2, wherein said acoustic lens is located relative to said ultrasound receiver such that the ultrasound exiting out of the lens surface of the acoustic lens is reflected from the ultrasound receiver, converged at the sample located between the acoustic lens and the ultrasound receiver and, after the ultrasound converged at and near the sample has been reflected from the lens surface of the acoustic lens, is vertically incident to the flat receiving surface.

4. The microscope according to claim 2, wherein, substantially at an intermediate area between a refractive convergence focal point where the ultrasound exiting from the lens surface of the acoustic lens is converged and a reflective convergence focal point where the ultrasound reflected from the flat receiving surface is converged, the flat receiving surface of the ultrasound receiver being located substantially perpendicular to a center axis of the acoustic lens, the sample being positioned at and near the reflective convergence focal point.

5. The microscope according to claim 2, wherein a sample support film is provided to locate the sample at an area between the lens surface of the acoustic lens and the flat receiving surface of the ultrasound wave receiver.

6. The microscope according to claim 5, wherein an X-Y scanning mechanism is provided to allow the sample support film to be moved in mutually orthogonal X-and Y-directions in a plane perpendicular to the center axis of the acoustic lens.

7. The microscope according claim 5, wherein an attitude adjusting mechanism is provided to adjust a tilt and a three-diamensional position of the sample support film.

8. The microscope according to claim 2, wherein a Z-axis mechanism is provided to allow the acoustic lens to be moved toward its set center axis position thereof.

9. The microscope according to claim 1, wherein:
 the ultrasound receiver and the beam conversion means comprise a phase conjugate mirror having a flat receiving surface which reflects but does not transmit the ultrasound therethrough, said phase conjugate mirror generating a phase conjugate wave of the ultrasound which is incident to the flat receiving surface thereof, the phase conjugate wave generated by the phase conjugate mirror being transmitted through the concave lens surface of the acoustic lens to the second electric/acoustic conversion means after being again transmitted through the sample; and
 the second electric/acoustic conversion means is shared by the first electric/acoustic conversion means.

10. The microscope according to claim 9, wherein said acoustic lens is located relative to said phase conjugated mirror such that the ultrasound exiting out of the concave lens surface of the acoustic lens is incident to the flat receiving surface to allow the phase conjugate wave which is generated for the phase conjugate mirror in accordance with the incident ultrasound to be converged at one of at the sample and near the sample located between the acoustic lens and the phase conjugate mirror and transmitting ultrasound which is obtained by a phase conjugate wave through the sample to be reflected back from the concave lens surface of the acoustic lens to be vertically incident to the flat ultrasound receiving surface.

11. The microscope according to claim 9, wherein, substantially at an intermediate area between a refractive convergence focal point where the ultrasound exiting from the concave lens surface of the acoustic lens is converged and a reflective convergence focal point where the ultrasound reflected form the concave lens surface of the acoustic lens is converged, the flat receiving surface of the phase conjugate mirror is perpendicular to a center axis of the acoustic lens, the sample being positioned at one of at the reflective convergence focal point and near the reflective convergence focal point.

12. The microscope according to claim 9, wherein said phase conjugate mirror comprises a piezoelectric element including said flat receiving surface and having an acoustically nonlinear characteristic, a pair of electrodes arranged in an opposed relation with the piezoelectric element sandwiched therebetween, and a voltage generator provided on one of the electrodes and adapted to apply a voltage to the one electrode.

13. The microscope according to claim 12, wherein said piezoelectric element is formed of a $NiNb_3O_5$ crystal.

14. The microscope according to claim 12, wherein said voltage generator applies a high frequency voltage to the one electrode, the high frequency voltage including a burst wave.

15. The microscope according to claim 9, wherein a sample support film is provided to locate the sample at an area between the concave lens surface of the acoustic lens and the flat receiving surface of the phase conjugate mirror.

16. The microscope according to claim 9, wherein an X-Y scanning mechanism is provided to allow the sample support film to be moved in mutually orthogonal X-and Y-directions in a plane perpendicular to a center axis of the acoustic lens.

17. The microscope according to claim 9, wherein an attitude adjusting mechanism is provided to adjust a tilt and a three-dimensional position of the sample support film.

18. The microscope according to claim 9, wherein a Z-axis mechanism is provided to allow the acoustic lens to be moved toward a set center axis position thereof.

19. An ultrasonic microscope comprising:
means for generating a high frequency signal;
first electric/acoustic conversion means for converting the high frequency signal to ultrasound;
an acoustic lens having an end surface to which the ultrasound coming from the first electric/acoustic conversion means is incident, the acoustic lens having a concave lens surface where the ultrasound coming from said end surface exits;
an ultrasound receiver having a flat receiving surface for reflecting at least a portion of the ultrasound exiting from said concave lens surface of the acoustic lens back to said concave lens surface, said flat receiving surface of said ultrasound receiver being positioned so that most of a reflective sound flux, corresponding to the reflected ultrasound, is converted by the ultrasound receiver to a parallel sound flux, when the reflective sound flux is reflected on the concave lens surface back to the flat receiving surface of the ultrasound receiver so that the parallel sound flux is substantially vertically incident to and is transmitted through the flat receiving surface;
second electric/acoustic converting means for converting the ultrasound transmitted through the ultrasound receiving surface into an electric signal, and for outputting the electric signal as an output reception signal; and
image forming means for forming an image based on the output reception signal output form the second electric/acoustic converting means.

20. An ultrasound microscope according to claim 19, wherein the ultrasound exiting form the concave lens surface of the acoustic lens is initially converged at one of a sample and near said sample, when said sample is positioned between the acoustic lens and the ultrasound receiver, and is converged again after the ultrasound is reflected form the flat receiving surface of the ultrasound receiver.

21. An ultrasound microscope according to claim 19, wherein the flat receiving surface of the ultrasound receiver is positioned substantially between a refractive convergence focal point where the ultrasound exiting from the concave lens surface of the acoustic lens is converged and a reflective convergence focal point where the ultrasound reflected from the concave lens surface of the acoustic lens is converged, the sample being positioned at one of the reflective convergence focal point and near said reflective convergence focal point.

22. An ultrasound microscope according to claim 19, wherein:
the ultrasound receiver is a phase conjugated mirror; and
the first electric/acoustic converting means also functions as the first electric/acoustic converting means.

23. A scanning acoustic microscope comprising:
means for generating a high frequency signal;
first electric/acoustic conversion means for converting the high frequency signal to ultrasound;
an acoustic lens having an end surface to which the ultrasound coming from the first electric/acoustic conversion means is incident and a concave lens surface where the ultrasound coming from the end surface exits;
beam conversion means having a flat surface for reflecting the ultrasound exiting from the acoustic lens, the flat surface being so positioned as to allow ultrasound which is transmitted through a sample to be converted to parallel beams in cooperation with the concave lens surface of the acoustic lens;
an ultrasound receiver having a receiving surface for allowing the ultrasound which is converted by the beam conversion means to the parallel beams, to be incident thereon substantially vertically;
second electric/acoustic conversion means for converting an ultrasound which is transmitted through the ultrasound receiver to an electrical signal and for generating a reception signal; and
image forming means for forming an image corresponding to the reception signal output from the second electric/acoustic conversion means; and
wherein:
the receiving surface of the ultrasound receiver is so formed as to be the same as the flat surface of the beam conversion means; and
the second electric/acoustic conversion means is provided on an end surface oppositely facing the receiving surface of the ultrasound receiver.

24. The microscope according to claim 23, wherein said acoustic lens is located relative to said ultrasound receiver such that the ultrasound exiting out of the lens surface of the acoustic lens is reflected form the ultrasound receiver, converged at one of said sample and near the sample located between the acoustic lens and the ultrasound receiver and, after the ultrasound converged at one of the sample and near the sample has been reflected from the lens surface of the acoustic lens, is vertically incident to the flat receiver surface.

25. The microscope according to claim 23, wherein, substantially at an intermediate area between a refractive convergency focal point where the ultrasound exiting from the lens surface of the acoustic lens is converged and a reflective convergency focal point where the ultrasound reflected from the flat receiving surface is converged, the flat receiving surface of the ultrasound receiver is located substantially perpendicular to a center axis of the acoustic lens, the sample being positioned at one of the reflective conveyance focal point and near the reflective conveyance focal point.

26. The microscope according to claim 23, wherein a sample support film is provided to locate the sample at an area between the lens surface of the acoustic lens and the flat receiving surface of the ultrasound receiver.

27. The microscope according to claim 26, wherein an X-Y scanning mechanism is provided to allow the sample support film to be moved in mutually orthogonal X-and Y-directions in a plane perpendicular to a center axis of the acoustic lens.

28. The microscope according to claim 26, wherein an attitude adjusting mechanism is provided to adjust a tilt and a three-dimensional position of the sample support film.

29. The microscope according to claim 23, wherein a Z-axis mechanism is provided to move the acoustic lens toward a set center axis position thereof.

* * * * *